(12) United States Patent
Chung et al.

(10) Patent No.: US 8,546,529 B2
(45) Date of Patent: *Oct. 1, 2013

(54) INJECTABLE BONE REGENERATION GEL CONTAINING BONE FORMATION ENHANCING PEPTIDE

(75) Inventors: Chong-Pyoung Chung, Seoul (KR); Yoon-Jeong Park, Seoul (KR); Jue-Yeon Lee, Gwacheon (KR)

(73) Assignees: Nano Intelligent Biomedical Engineering Corporation Co., Ltd., Seoul (KR); Seoul National University Industry Foundation, Seoul (KR)

( * ) Notice: Subject to any disclaimer, the term of this patent is extended or adjusted under 35 U.S.C. 154(b) by 503 days.

This patent is subject to a terminal disclaimer.

(21) Appl. No.: 12/663,399

(22) PCT Filed: Jun. 5, 2008

(86) PCT No.: PCT/KR2008/003165
§ 371 (c)(1),
(2), (4) Date: Aug. 5, 2010

(87) PCT Pub. No.: WO2008/150119
PCT Pub. Date: Dec. 11, 2008

(65) Prior Publication Data
US 2010/0317587 A1    Dec. 16, 2010

(30) Foreign Application Priority Data
Jun. 5, 2007 (KR) .................. 10-2007-0055211

(51) Int. Cl.
| C07K 7/00 | (2006.01) |
| C07K 7/06 | (2006.01) |
| C07K 7/08 | (2006.01) |
| C07K 14/00 | (2006.01) |
| A61K 38/00 | (2006.01) |

(52) U.S. Cl.
USPC ........... 530/329; 530/324; 530/326; 530/327; 514/16.7

(58) Field of Classification Search
USPC ................. 530/324, 326, 327, 329; 514/16.7
See application file for complete search history.

(56) References Cited

U.S. PATENT DOCUMENTS

| 6,509,026 | B1 * | 1/2003 | Ashkar et al. ................. 424/422 |
| 7,241,873 | B2 * | 7/2007 | Uede et al. ................. 530/387.3 |
| 2004/0234524 | A1 * | 11/2004 | Uede et al. ................. 424/145.1 |
| 2006/0002923 | A1 * | 1/2006 | Uede et al. ................. 424/143.1 |
| 2009/0238875 | A1 * | 9/2009 | Noh et al. ..................... 424/487 |

FOREIGN PATENT DOCUMENTS

| JP | 2000-143697 A | 5/2000 |
| JP | 2003-038635 A | 2/2003 |
| KR | 10-0630903 | 10/2006 |
| KR | 10-0676945 | 2/2007 |
| WO | WO 02/081522 | * 10/2002 |
| WO | WO 03/023401 | * 3/2003 |
| WO | WO 03/027151 | * 4/2003 |
| WO | WO 2005/089826 | * 9/2005 |
| WO | WO 2007/089084 | * 8/2007 |

OTHER PUBLICATIONS

International Search Report from PCT/KR2008/003165; Jul. 2008.

* cited by examiner

Primary Examiner — Amber D Steele
(74) Attorney, Agent, or Firm — Rabin & Berdo, P.C.

(57) ABSTRACT

The present invention relates to an injectable bone regeneration material containing a bone formation enhancing peptide, and more particularly, to an injectable bone regeneration material, in which a bone formation enhancing peptide essentially containing one and more amino acid sequences among SEQ ID NO: 1 to SEQ ID NO: 28 is bonded or mixed to a gel-forming base material selected from the group consisting of chitosan, alginic acid, silk fibroin, propylene glycol, propylene glycol alginic acid, poloxamer, chondroitin sulphate, and the combination thereof. The injectable bone regeneration material according to the present invention can increase differentiation of bone marrow stromal cells and osteoblasts into bone tissue, thus maximizing tissue regeneration by a peptide capable of promoting differentiation of bone tissue and periodontal tissue regeneration. The injectable bone regeneration material is in the form of a gel, and thus can be applied to a surface of various medical devices such as implant etc., and can be mixed with bone graft particles to apply, so that it can increase a treatment effect of existing medical devices to maximize a tissue regeneration effect.

12 Claims, 3 Drawing Sheets

SEQUENCE LISTING

```
<160> NUMBER OF SEQ ID NOS: 28

<210> SEQ ID NO 1
<211> LENGTH: 8
<212> TYPE: PRT
<213> ORGANISM: Oryctolagus cuniculus

<400> SEQUENCE: 1

Tyr Arg Leu Lys Arg Ser Lys Ser
1               5

<210> SEQ ID NO 2
<211> LENGTH: 13
<212> TYPE: PRT
<213> ORGANISM: Oryctolagus cuniculus

<400> SEQUENCE: 2

Lys Met Phe His Val Ser Asn Ala Gln Tyr Pro Gly Ala
1               5                   10

<210> SEQ ID NO 3
<211> LENGTH: 21
<212> TYPE: PRT
<213> ORGANISM: Oryctolagus cuniculus

<400> SEQUENCE: 3

Tyr Arg Leu Lys Arg Ser Lys Ser Lys Met Phe His Val Ser Asn Ala
1               5                   10                  15

Gln Tyr Pro Gly Ala
            20

<210> SEQ ID NO 4
<211> LENGTH: 7
<212> TYPE: PRT
<213> ORGANISM: Homo sapiens

<400> SEQUENCE: 4

Tyr Gly Leu Arg Ser Lys Ser
```

-continued

<210> SEQ ID NO 5
<211> LENGTH: 14
<212> TYPE: PRT
<213> ORGANISM: Homo sapiens

<400> SEQUENCE: 5

Lys Lys Phe Arg Arg Pro Asp Ile Gln Tyr Pro Asp Ala Thr
1               5                   10

<210> SEQ ID NO 6
<211> LENGTH: 21
<212> TYPE: PRT
<213> ORGANISM: Homo sapiens

<400> SEQUENCE: 6

Tyr Gly Leu Arg Ser Lys Ser Lys Lys Phe Arg Arg Pro Asp Ile Gln
1               5                   10                  15

Tyr Pro Asp Ala Thr
            20

<210> SEQ ID NO 7
<211> LENGTH: 17
<212> TYPE: PRT
<213> ORGANISM: Homo sapiens

<400> SEQUENCE: 7

Ala Lys His Lys Gln Arg Lys Arg Leu Lys Ser Ser Cys Lys Arg His
1               5                   10                  15

Pro

<210> SEQ ID NO 8
<211> LENGTH: 17
<212> TYPE: PRT
<213> ORGANISM: Homo sapiens

<400> SEQUENCE: 8

Ser Asp Val Gly Trp Asn Asp Trp Ile Val Ala Pro Pro Gly Tyr His
1               5                   10                  15

Ala

<210> SEQ ID NO 9
<211> LENGTH: 25
<212> TYPE: PRT
<213> ORGANISM: Homo sapiens

<400> SEQUENCE: 9

Cys Pro Phe Pro Leu Ala Asp His Leu Asn Ser Thr Asn His Ala Ile
1               5                   10                  15

Val Gln Thr Leu Val Asn Ser Val Asn
            20                  25

<210> SEQ ID NO 10
<211> LENGTH: 20
<212> TYPE: PRT
<213> ORGANISM: Homo sapiens

<400> SEQUENCE: 10

Lys Ile Pro Lys Ala Cys Cys Val Pro Thr Glu Leu Ser Ala Ile Ser
1               5                   10                  15

Met Leu Tyr Leu
            20

```
<210> SEQ ID NO 11
<211> LENGTH: 18
<212> TYPE: PRT
<213> ORGANISM: Homo sapiens

<400> SEQUENCE: 11

Ser Met Leu Tyr Leu Asp Glu Asn Glu Lys Val Val Leu Lys Asn Tyr
1               5                   10                  15

Gln Asp

<210> SEQ ID NO 12
<211> LENGTH: 20
<212> TYPE: PRT
<213> ORGANISM: Homo sapiens

<400> SEQUENCE: 12

Gln Ala Lys His Lys Gln Arg Lys Arg Leu Lys Ser Ser Gly Lys Arg
1               5                   10                  15

His Pro Leu Tyr
            20

<210> SEQ ID NO 13
<211> LENGTH: 19
<212> TYPE: PRT
<213> ORGANISM: Homo sapiens

<400> SEQUENCE: 13

Asp His Leu Asn Ser Thr Asn His Ala Ile Val Gln Thr Leu Val Asn
1               5                   10                  15

Ser Val Asn

<210> SEQ ID NO 14
<211> LENGTH: 21
<212> TYPE: PRT
<213> ORGANISM: Homo sapiens

<400> SEQUENCE: 14

Ser Met Leu Tyr Leu Asp Glu Asn Glu Lys Val Val Leu Lys Asn Tyr
1               5                   10                  15

Gln Asp Met Val Val
            20

<210> SEQ ID NO 15
<211> LENGTH: 10
<212> TYPE: PRT
<213> ORGANISM: Homo sapiens

<400> SEQUENCE: 15

Arg Lys Lys Asn Lys Asn Cys Arg Arg His
1               5                   10

<210> SEQ ID NO 16
<211> LENGTH: 21
<212> TYPE: PRT
<213> ORGANISM: Homo sapiens

<400> SEQUENCE: 16

Ser Ser Ile Pro Lys Ala Cys Cys Val Pro Thr Glu Leu Ser Ala Ile
1               5                   10                  15

Ser Met Leu Tyr Leu
            20
```

<210> SEQ ID NO 17
<211> LENGTH: 18
<212> TYPE: PRT
<213> ORGANISM: Homo sapiens

<400> SEQUENCE: 17

Pro Lys His His Ser Gln Arg Ala Arg Lys Lys Asn Lys Asn Cys Arg
1               5                   10                  15

Arg His

<210> SEQ ID NO 18
<211> LENGTH: 20
<212> TYPE: PRT
<213> ORGANISM: Homo sapiens

<400> SEQUENCE: 18

Leu Val Asn Ser Val Asn Ser Ser Ile Pro Lys Ala Cys Cys Val Pro
1               5                   10                  15

Thr Glu Leu Ser
            20

<210> SEQ ID NO 19
<211> LENGTH: 21
<212> TYPE: PRT
<213> ORGANISM: Homo sapiens

<400> SEQUENCE: 19

Ser Met Leu Tyr Leu Asp Glu Tyr Asp Lys Val Val Leu Lys Asn Tyr
1               5                   10                  15

Gln Glu Met Val Val
            20

<210> SEQ ID NO 20
<211> LENGTH: 20
<212> TYPE: PRT
<213> ORGANISM: Homo sapiens

<400> SEQUENCE: 20

Tyr Val Pro Lys Pro Cys Cys Ala Pro Thr Lys Leu Asn Ala Ile Ser
1               5                   10                  15

Val Leu Tyr Phe
            20

<210> SEQ ID NO 21
<211> LENGTH: 23
<212> TYPE: PRT
<213> ORGANISM: Homo sapiens

<400> SEQUENCE: 21

Val Ser Ser Ala Ser Asp Tyr Asn Ser Ser Glu Leu Lys Thr Ala Cys
1               5                   10                  15

Arg Lys His Glu Leu Tyr Val
            20

<210> SEQ ID NO 22
<211> LENGTH: 19
<212> TYPE: PRT
<213> ORGANISM: Homo sapiens

<400> SEQUENCE: 22

Tyr Val Pro Lys Pro Cys Cys Ala Pro Thr Lys Leu Asn Ala Ile Ser
1               5                   10                  15

```
Val Leu Tyr

<210> SEQ ID NO 23
<211> LENGTH: 23
<212> TYPE: PRT
<213> ORGANISM: Homo sapiens

<400> SEQUENCE: 23

Val Leu Tyr Phe Asp Asp Asn Ser Asn Val Ile Leu Lys Lys Tyr Arg
1               5                   10                  15

Asn Met Val Val Arg Ala Cys
            20

<210> SEQ ID NO 24
<211> LENGTH: 20
<212> TYPE: PRT
<213> ORGANISM: Homo sapiens

<400> SEQUENCE: 24

Thr Val Pro Lys Pro Cys Cys Ala Pro Thr Gln Leu Asn Ala Ile Ser
1               5                   10                  15

Val Leu Tyr Phe
            20

<210> SEQ ID NO 25
<211> LENGTH: 21
<212> TYPE: PRT
<213> ORGANISM: Homo sapiens

<400> SEQUENCE: 25

Glu Asn Ser Ser Ser Asp Gln Arg Gln Ala Cys Lys Lys His Glu Leu
1               5                   10                  15

Tyr Val Ser Phe Arg
            20

<210> SEQ ID NO 26
<211> LENGTH: 21
<212> TYPE: PRT
<213> ORGANISM: Homo sapiens

<400> SEQUENCE: 26

Thr Val Pro Lys Pro Cys Cys Ala Pro Thr Gln Leu Asn Ala Ile Ser
1               5                   10                  15

Val Leu Tyr Phe Asp
            20

<210> SEQ ID NO 27
<211> LENGTH: 20
<212> TYPE: PRT
<213> ORGANISM: Homo sapiens

<400> SEQUENCE: 27

Ile Ser Val Leu Tyr Phe Asp Asp Ser Ser Asn Val Ile Leu Lys Lys
1               5                   10                  15

Tyr Arg Asn Met
            20

<210> SEQ ID NO 28
<211> LENGTH: 28
<212> TYPE: PRT
<213> ORGANISM: Homo sapiens

<400> SEQUENCE: 28
```

```
-continued

Gly Leu Arg Ser Lys Ser Lys Lys Phe Arg Arg Pro Asp Ile Gln Tyr
1               5                   10                  15

Pro Asp Ala Thr Asp Glu Asp Ile Thr Ser His Met
            20              25
```

INJECTABLE BONE REGENERATION GEL CONTAINING BONE FORMATION ENHANCING PEPTIDE

CROSS REFERENCE TO RELATED APPLICATION

This application is a 371 National Stage of PCT Application No. PCTKR2008/003165, filed on Jun. 5, 2008, which claims the benefit under 35 U.S.C. §119 (a) of Korean Patent Application No. 10-2007-0055211, filed on Jun. 5, 2007, the entire contents of which are incorporated herein by reference.

TECHNICAL FIELD

The present invention relates to an injectable bone regeneration material containing a bone formation enhancing peptide, and more particularly, to an injectable bone regeneration material, in which a bone formation enhancing peptide consisting essentially of one or more amino acid sequences among SEQ ID NO: 1 to SEQ ID NO: 28 is bonded or mixed to a gel-forming base material selected from the group consisting of chitosan, alginic acid, silk fibroin, propylene glycol, propylene glycol alginic acid, poloxamer, chondroitin sulphate, and the combination thereof.

BACKGROUND ART

In the fields of dentistry, orthopedics and plastic surgery, various regeneration techniques are used for recovering lost bone tissue and a bone defect after treating tumor. The regeneration techniques include guided bone tissue regeneration using a bone graft material with various shapes and a barrier membrane, autogenous and allogeneic bone grafts, etc., and recently methods using various kinds of growth factors, protein, and the like are studied. The supply of xenogeneic bone and alloplastic bone, which are used as a bone graft material, has been dependent upon imports so far, but lately, domestically produced bone grafts are being marketed due to strengthening of domestic technologies. However, since the shape of a bone defect is irregular, a graft material, which can completely fill the bone defect, has not yet been developed. In addition, there was a limitation in that, when a biomaterial itself, such as a bone graft or a barrier membrane is used as a graft material, it may function as a carrier having bone conductivity, but it does not have osteoconductivity for initial osteogenesis, which is essential to shorten the treatment period, and thus osteogenesis can be induced after a considerable period of time after surgical operations.

In order to increase graft performance, physiologically active substances inducing chemotaxis, for example, extracellular matrix proteins, tissue growth factors, or bone morphogenetic proteins, have been experimentally used to provide rapid osteogenesis, but the use of such proteins has problems in that the proteins are relatively expensive, cause immune responses or have a short in vivo half-life. Also since the proteins are exposed to systemic blood flow when applied in vivo, such that it is difficult to maintain their effective concentrations at local sites, they must be administered with high dosage for maintaining their effective concentrations in vivo, which caused concerns raised over side effects due to high dose administration. For these reasons, a novel technology capable of overcoming such problems is required.

As the only bone tissue regeneration-inducing material currently marketed, there is Emdogain (Straumann), and it consists of enamel matrix derivative, especially amelogenin to induce natural growth of teeth, thus inhibiting epithelial tissue formation in a defect and forming a novel alveolar bone and cementum. However, amelogenin is a protein so it dissolves at room temperature, and at present, it is extracted from developing tooth germs of 6-month-old porcine fetuses and thus there is a possibility of inducing immune responses when it is applied to humans, the production efficiency is low, and the cost is high.

Accordingly, the present inventors have made extensive efforts to solve the above-described problems occurring in the prior art and, as a result, have developed an injectable bone regeneration material containing a bone formation enhancing peptide derived from extracellular matrix and confirmed that it has the ability to differentiate into bone tissue and bone-regenerating ability in a bone defect, thereby completing the present invention.

SUMMARY OF INVENTION

It is an object of the present invention to provide an injectable bone regeneration material, in which a bone formation enhancing peptide is bonded to a gel-forming base material.

Another object of the present invention is to provide a method for preparing an injectable bone regeneration material containing a bone formation enhancing peptide.

To achieve the above objects, the present invention provides an injectable bone regeneration material, in which a bone formation enhancing peptide consisting essentially of one or more amino acid sequences among SEQ ID NO: 1 to SEQ ID NO: 28 is bonded or mixed to a gel-forming base material selected from the group consisting of chitosan, alginic acid, silk fibroin, propylene glycol, propylene glycol alginic acid, poloxamer, chondroitin sulphate, and the combination thereof.

In the present invention, it is preferably that the bone formation enhancing peptide is covalently bonded or physically mixed to the gel-forming base material.

In the present invention, the bone regeneration material is preferably for periodontal and orthopedic operations. Also the bone regeneration material is preferably for bone tissue repair or bone tissue regeneration.

In addition, the present invention provides a method for preparing an injectable bone regeneration material, which comprises the steps of (a) preparing a gel-forming base material selected from the group consisting of chitosan, alginic acid, silk fibroin, propylene glycol, propylene glycol alginic acid, poloxamer, chondroitin sulphate, and the combination thereof; and (b) gelling by adding a bone formation enhancing peptide consisting essentially of one or more amino acid sequence among SEQ ID NO: 1 to SEQ ID NO: 28 to the gel-forming base material.

Other features and aspects of the present invention will be apparent from the following detailed description and the appended claims.

DETAILED DESCRIPTION OF THE INVENTION AND PREFERRED EMBODIMENTS

Figure 1:
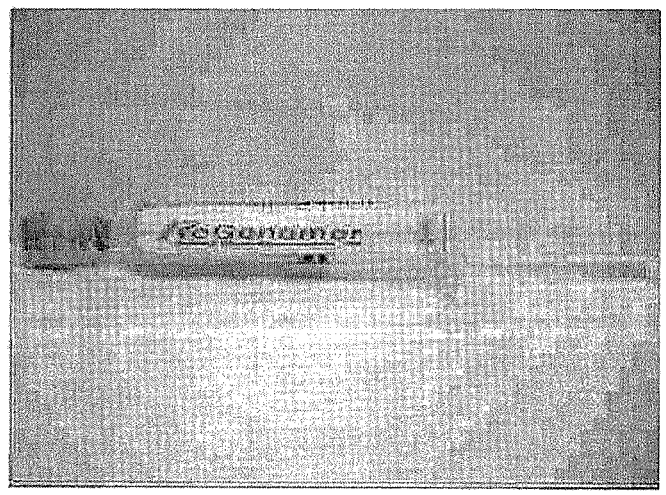
FIG. 1 shows a photograph of a bone regeneration material containing an injectable bone formation enhancing peptide according to the present invention.

The present invention relates to an injectable bone regeneration material, in which a bone formation enhancing peptide consisting essentially of one or more amino acid sequences among SEQ ID NO: 1 to SEQ ID NO: 28 is bonded or mixed to a gel-forming base material selected from the group consisting of chitosan, alginic acid, silk fibroin, propylene glycol, propylene glycol alginic acid, poloxamer, chondroitin sulphate, and the combination thereof.

In order to develop the bone formation enhancing peptide according to the present invention, active site amino acid sequence is isolated and extracted from a protein comprising an extracellular matrix, and then subjected to chemical modification so as to maintain the active structure thereof.

Particularly, the peptide preferably contains any one amino acid sequence selected from the group consisting of: an amino acid sequence of positions 85-92 of bone sialoprotein 1 (BSP 1) of a rabbit: YRLKRSKS (SEQ ID NO: 1), an amino acid sequence of positions 93-105 of bone sialoprotein 1 (BSP 1) of a rabbit: KMFHVSNAQYPGA (SEQ ID NO: 2), an amino acid sequence of positions 85-105 of bone sialoprotein 1 (BSP 1) of a rabbit: YRLKRSKSKMFHVSNAQYPGA (SEQ ID NO: 3), an amino acid sequence of positions 149-155 of haman bone sialoprotein I: YGLRSKS (SEQ ID NO: 4), an amino acid sequence of positions 156-169 of haman bone sialoprotein I: KKFRRPDIQYPDAT (SEQ ID NO: 5), an amino acid sequence of positions 149-169 of haman bone sialoprotein I: YGLRSKSKKFRRPDIQYPDAT (SEQ ID NO: 6), an amino acid sequence of positions 284-300 of human bone morphogenetic protein (BMP-2): AKHKQRKRLKSSCKRHP (SEQ ID NO: 7), an amino acid sequence of positions 306-322 of human bone morphogenetic protein (BMP-2): SDVGWNDWIVAPPGYHA (SEQ ID NO: 8), an amino acid sequence of positions 329-353 of human bone morphogenetic protein (BMP-2): CPFPLADHLNSTNHAIVQTLVNSVN (SEQ ID NO: 9), an amino acid sequence of positions 355-374 of human bone morphogenetic protein (BMP-2): KIPKACCVPTELSAISMLYL (SEQ ID NO: 10), an amino acid sequence of positions 370-387 of human bone morphogenetic protein (BMP-2): SMLYLDENEKVVLKNYQD (SEQ ID NO: 11), an amino acid sequence of positions 283-302 of human bone morphogenetic protein (BMP-2): QAKHKQRKRLKSSGKRHPLY (SEQ ID NO: 12), an amino acid sequence of positions 335-353 of human bone morphogenetic protein (BMP-2): DHLNSTNHAIVQTLVNSVN (SEQ ID NO: 13), an amino acid sequence of positions 370-390 of human bone morphogenetic protein (BMP-2): SMLYLDENEKVVLKNYQDMVV (SEQ ID NO: 14); an amino acid sequence of positions 302-311 of human bone morphogenetic protein (BMP-4): RKKNKNCRRH (SEQ ID NO: 15), an amino acid sequence of positions 366-386 of human bone morphogenetic protein (BMP-4): SSIPKACCVPTELSAISMLYL (SEQ ID NO: 16), an amino acid sequence of positions 294-311 of human bone morphogenetic protein (BMP-4): PKHHSQRARKKNKNCRRH (SEQ ID NO: 17), an amino acid sequence of positions 360-379 of human bone morphogenetic protein (BMP-4): LVNSVNSSIPKACCVPTELS (SEQ ID NO: 18), an amino acid sequence of positions 382-402 of human bone morphogenetic protein (BMP-4): SMLYLDEYDKVVLKNYQEMVV (SEQ ID NO: 19); an amino acid sequence of positions 472-491 of human bone morphogenetic protein (BMP-6): YVPKPCCAPTKLNAISVLYF (SEQ ID NO: 20), an amino acid sequence of positions 397-419 of human bone morphogenetic protein (BMP-6): VSSASDYNSSELKTACRKHELYV (SEQ ID NO: 21), an amino acid sequence of positions 472-490 of human bone morphogenetic protein (BMP-6): YVPKPCCAPTKLNAISVLY (SEQ ID NO: 22), an amino acid sequence of positions 488-510 of human bone morphogenetic protein (BMP-6): VLYFDDNSNVILKKYRNMVVRAC (SEQ ID NO: 23); an amino acid sequence of positions 390-409 of human bone morphogenetic protein (BMP-7): TVPKPCCAPTQLNAISVLYF (SEQ ID NO: 24), an amino acid sequence of positions 320-340 of human bone morphogenetic protein (BMP-7): ENSSSDQRQACKKHELYVSFR (SEQ ID NO: 25), an amino acid sequence of positions 390-410 of human bone morphogenetic protein (BMP-7): TVPKPCCAPTQLNAISVLYFD (SEQ ID NO: 26), an amino acid sequence of positions 404-423 of human bone morphogenetic protein (BMP-7): ISVLYFDDSSNVILKKYRNM (SEQ ID NO: 27), and an amino acid sequence of positions 150-177 of haman bone sialoprotein I (Osteopontin): GLRSKSKKFRRPDIQYPDATDEDITSHM (SEQ ID NO: 28).

The injectable bone regeneration material according to the present invention can maximize tissue regeneration by increasing differentiation of bone marrow stromal cells and osteoblasts in a defect into bone tissue using a peptide capable of promoting differentiation of bone tissue and periodontal tissue regeneration.

In addition, the bone formation enhancing peptide is preferably contained in the bone regeneration material in an amount of 30-120 mg per ml of the bone regeneration material. More preferably, the peptide consists of SEQ ID NO: 6 and is contained in an amount of 50-100 mg per g of the bone regeneration material.

In an embodiment of the present invention, the method of introducing a peptide into a gel base include a method in which a peptide and an alginate solution are mixed to prepare and a method in which an ester bond between peptide and alginate is formed by a cross-linker to obtain a conjugate solution of peptide-alginate, thus further adding peptide thereto to prepare.

As a base material usable in the present invention, it is preferable to use chitosan, alginic acid, silk fibroin, propylene glycol, propylene glycol alginic acid, poloxamer, chondroitin sulphate, and the like, and the base material is in the form of a gel for easy injection. Among them, the alginic acid is a biocompatible and nontoxic polysaccharide, and many studies has been conducted on various uses thereof as a biomaterial such as drug delivery system, a carrier for cell transplantation, a wound treatment agent etc.

The bone regeneration material containing a bone formation enhancing peptide according to the present invention can be used alone or in combination with bone graft implant particles, and the bone graft particles include organism-derived bone mineral powder and porous blocks thereof, synthetic hydroxyapatite powder and porous blocks thereof, tricalcium phosphate powder and porous blocks thereof, monocalcium phosphate powder and porous blocks thereof.

In an embodiment of the present invention, it is preferable to use alginic acid at a concentration of 5-10% (w/v), and more preferably 6-8% (w/v), for preparing a bone regeneration material for easy injection. In order to provide calcium and phosphate, which are inorganic ions necessary for bone regeneration, alginic acid was dissolved in a tripolyphosphate solution, then added with calcium sulfate. It is preferable to use tripolyphosphate at a concentration of 1-10% (w/v), and more preferably 4-6% (w/v). The calcium sulfate is preferably added at a concentration of 1~20 mg/mL, and more preferably added at a concentration of 2~10 mg/mL.

Moreover, an injectable gel for bone regeneration according to the present invention can be applied to a surface of various medical devices such as implant, etc., and can be mixed with bone graft particles to apply, so that it can increase a therapeutic effect of existing medical devices to maximize a tissue regeneration effect, thus it can be utilized in rapid recovery of defects in the field of dentistry as well as in the fields of bone tissue repair in tumor patients, orthopedics, and plastic surgery.

EXAMPLES

Hereinafter, the present invention will be described in further detail with reference to examples. It is to be understood, however, that these examples are for illustrative purposes only and are not to be construed to limit the scope of the present invention.

Example 1

Incorporation of Bone Formation Enhancing Peptide into Sodium Alginate

A bone formation enhancing peptide used in this Example was a peptide of SEQ ID NO: 6. 7 g of sodium alginate (Sigma) was dissolved in 100 mL of 5% (w/v) tripolyphosphate, and then, autoclaved. 50 mg of calcium sulfate was added to 10 mL of the above solution and well mixed. 1 g of bone formation enhancing peptide was added and well mixed, and then injected into a syringe (FIG. 1).

Example 2

Covalent Bond of Bone Formation Enhancing Peptide to Sodium Alginate

Sodium alginate was dissolved in a 0.1M MES buffer (0.1M MES, morpholinoethane sulfonic acid, 0.3M NaCl, pH 6.5) at a concentration of 1% (w/v, 100 mg/100 mL). 1-ethyl-3-(3-dimethylaminopropyl) carbodiimide (EDC) (50 mg EDC/g alginate) and N-hydroxysulfosuccinimide(sulfo-NHS)(28 mg sulfo-NHS/g alginate) were added and allowed to react with stirring for 30 minutes, thus activating carboxylic acid group of alginate. Peptides were added thereto at a certain ratio and allowed to react with stirring at room temperature for 24 hours. Buffer salts, reaction byproducts and unreacted peptides were removed from a reaction solution in deionized water for 24 hours with dialysis tubing (MWCO 3500), and a solvent was removed by lyophilizing, thus obtaining peptide-sodium alginate.

7 g of the obtained peptide-sodium alginate was dissolved in 100 mL of 5% (w/v) tripolyphosphate, and 50 mg of calcium sulfate was added to 10 mL of the resulting solution, and then well-mixed. 1 g of bone formation enhancing peptide was added and well mixed, and then injected into a syringe.

Experimental Example 1

Cell Adhesion to Injectable Bone Regeneration Materials According to the Present Invention Injectable bone regeneration materials prepared in Example 1 were put into 4 wells to inoculate cells on them, then cells were cultured for 24 hours. Human osteosarcoma cells were obtained from Korean Cell Line Bank (KCLB No. 21543) to use. Bone regeneration materials, into which the cells were inoculated to culture, were fixed with 2% glutaraldehyde solution. The fixed bone regeneration materials were treated with 1% triton X-100, and then cell nuclei were stained with DAPI (Molecular Probe, blue) and actins were stained with Alexa Flour 488 (Molecular Probe, green). Focal adhesion was primarily stained with Rabbit primary vincluin antibody (Sigma) and then secondarily stained with Alexa Fluor 568 mouse anti-rabbit IgG (Molecular Probe, red). After staining, the cells attached to the bone regeneration materials were washed to observe with a confocal laser scanning fluorescence microscope.

Figure 2:
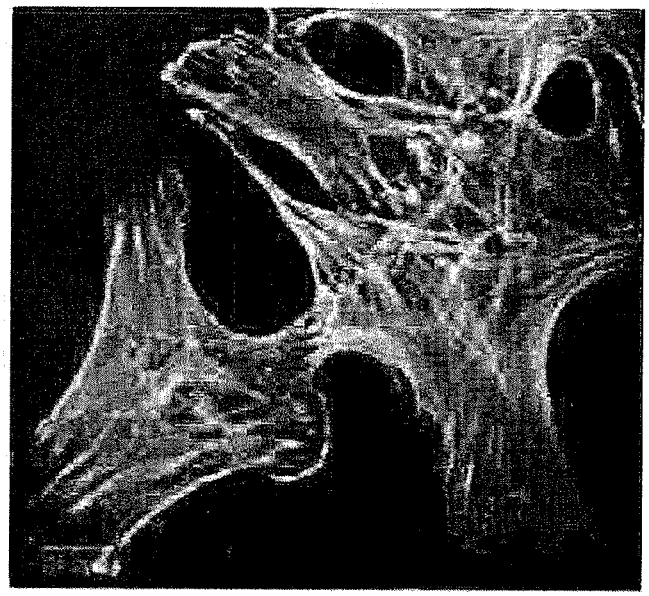
FIG. 2 illustrates a confocal laser scanning fluorescence microphotograph showing the pattern of cell adhesion to an injectable bone regeneration material containing a bone formation enhancing peptide according to the present invention.
Figure 3:
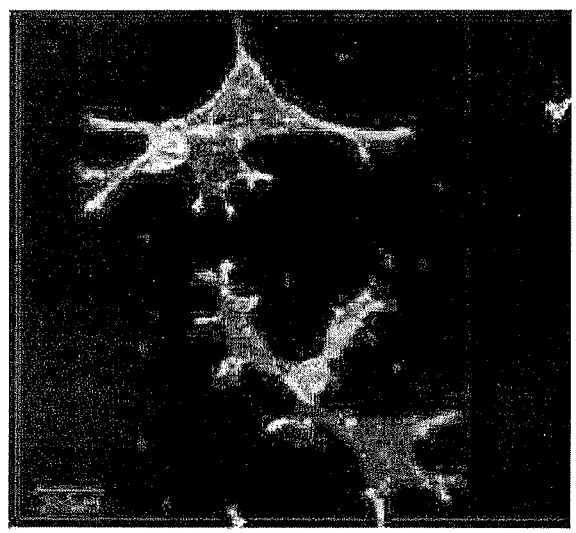
FIG. 3 illustrates a confocal laser scanning fluorescence microphotograph showing the pattern of cell adhesion to an injectable bone regeneration material containing no bone formation enhancing peptide.

FIG. 2 shows cells attached to a bone regeneration material containing bone formation enhancing peptide, and FIG. 3 shows cells attached to a bone regeneration material containing no bone formation enhancing peptide. It was observed that the pattern of cell adhesion in FIG. 3 was spherical forms and thus it could not form stable adhesion, whereas, in FIG. 2, it was observed that actin stress fibers were already extended in most of cells after 24 hour, focal adhesion was formed well and the like, suggesting that the cells stably adhered to the bone regeneration materials.

Experimental Example 2

Calcification of Cells by Bone Regeneration Materials According to the Present Invention Mesodermal stem cells $C_2C_{12}$ (America Type Culture Collection, CRL-1772) were cultured for 14 days, while adding the injectable bone regeneration materials prepared in Example 1 to a medium for hard tissue formation, containing calcein (fluorescent substance for calcium). The cultured osteoblasts were fixed with 2% glutaraldehyde solution. The fixed cells were treated with 1% triton X-100, and then nuclei were strained with DAPI (blue) and actins were stained with Rhodamine phalloidin (Molecular Probe, red), thus staning the cultured cells. After the staining, the samples were washed and fixed, and then calcium deposited on extracellular matrixes was observed with a confocal laser fluorescence scanning microscope.

Figure 4:
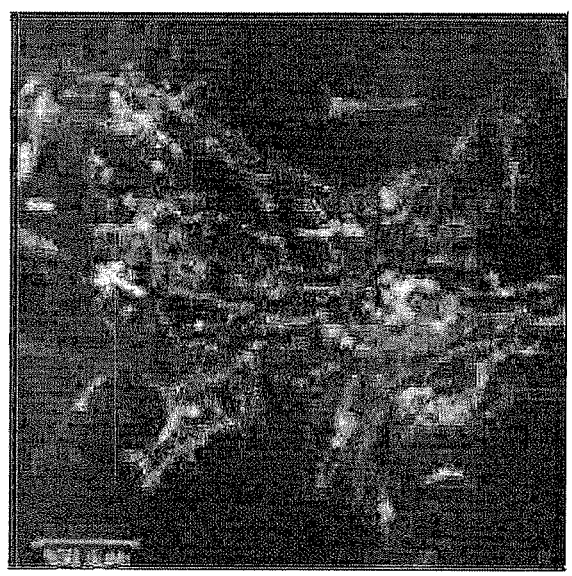
FIG. 4 illustrates a confocal laser scanning fluorescence microphotograph showing the degree of calcification on an injectable bone regeneration material containing a bone formation enhancing peptide.
Figure 5:
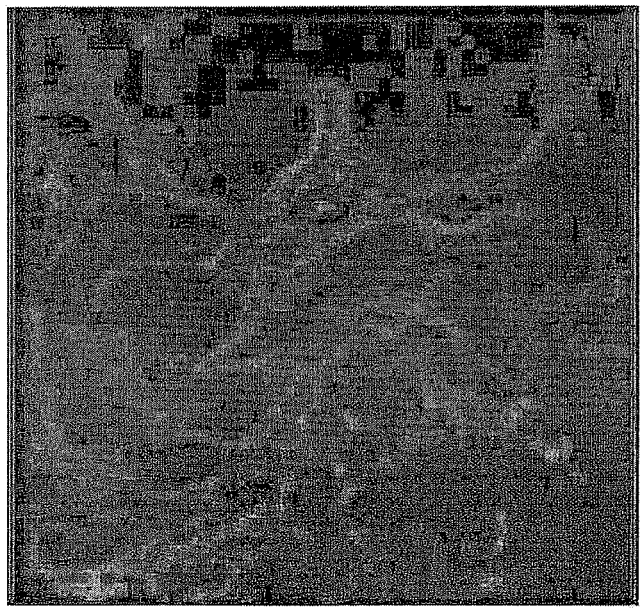
FIG. 5 illustrates a confocal laser scanning fluorescence microphotograph showing the degree of calcification on an injectable bone regeneration material containing no bone formation enhancing peptide.

FIG. 4 shows a bone regeneration material containing a bone formation enhancing peptide, and FIG. 5 shows a bone regeneration material containing no bone formation enhancing peptide. As shown in FIGS. 4 and 5, in the case of the bone regeneration material containing a bone formation enhancing peptide, much more calcium fluorescence appeared. From this result, it could be confirmed that the bone formation enhancing peptide promotes calcification of cells.

Experimental Example 3

Effect of Inventive Bone Regeneration Material on Regeneration of Rabbit Cranial Bone At the cranial sites of New Zealand white rabbits (species name: *Cuniculus*), a circular bone defect having a diameter of 8 mm was formed, and the bone regeneration material prepared in Example 1 were grafted into the bone defects in an amount of 0.2 mL/defect, and the bone membrane and the skin were double sutured to each other. At 4 weeks after the grafting, the animals were sacrificed, and samples collected from the animals were fixed in formalin solution. Then, the tissues were embedded so as to prepare samples having a thickness of 20 μm. The prepared samples were stained with basic fuchsine and toluidine blue, thus constructing non-decalcified samples. The constructed samples were photographed with an optical microscope.

Figure 6:
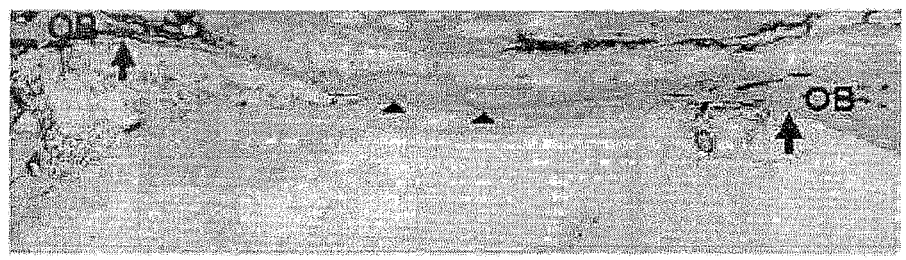
FIG. 6 shows the bone regeneration effect at 4th week after transplanting an injectable bone regeneration material containing no bone formation enhancing peptide into bone defects in the rabbit cranial bone.
Figure 7:
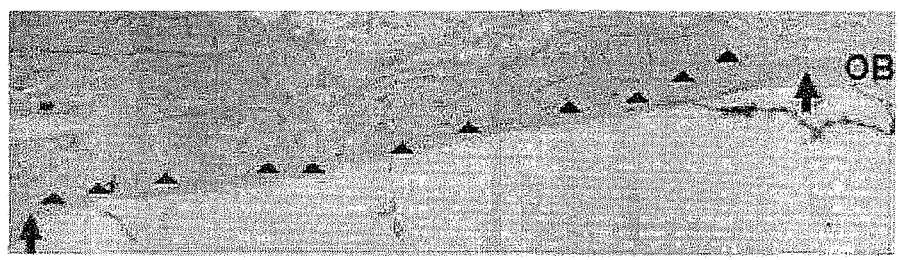
FIG. 7 shows the bone regeneration effect at 4th week after transplanting an injectable bone regeneration material containing a bone formation enhancing peptide into bone defects in the rabbit cranial bone.

FIG. 6 shows a group grafted with the bone regeneration materials without peptide, and FIG. 7 shows a group grafted with the bone regeneration materials containing the bone formation enhancing peptide. As shown in FIGS. 6 and 7, it was found that, in the case of the bone regeneration material containing a bone formation enhancing peptide, much more newborn bones were formed to the center of bone defect.

INDUSTRIAL APPLICABILITY

As described in detail above, the present invention has an effect of providing an injectable bone regeneration material containing a bone formation enhancing peptide, and a method for preparing an injectable bone regeneration material containing a bone formation enhancing peptide. The injectable bone regeneration material according to the present invention increases differentiation rate of regeneration-associated cells into bone tissue by bone formation enhancing peptide to maximize tissue regeneration, can be locally applied in periodontal and orthopedic operations, and can be used in rapid bone tissue regeneration in defects caused by a disease and an external wound.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

---

What is claimed is:

1. An injectable bone regeneration material comprising (a) one or more bone formation enhancing peptides consisting essentially of SEQ ID NO: 4, SEQ ID NO: 5, SEQ ID NO: 6 or SEQ ID NO: 28 and (b) a gel-forming base material selected from the group consisting of chitosan, alginic acid, silk fibroin, propylene glycol, propylene glycol alginic aid, poloxamer, chondroitin sulphate, and combinations thereof wherein the bone formation enhancing peptide(s) is bonded or mixed to the gel-forming base material.

2. The injectable bone regeneration material according to claim 1, wherein the bone formation enhancing peptide is covalently bonded or physically mixed to the gel-forming base material.

3. The injectable bone regeneration material according to claim 1, which is used for periodontal and orthopedic operations.

4. The injectable bone regeneration material according to claim 1, which is used for bone tissue repair or bone tissue regeneration.

5. A method to promote bone regeneration in a patient in need of periodontal and/or orthopedic bone regeneration comprising administration to said patient of the bone regeneration material of claim 1, wherein said one or more amino acid sequences is SEQ ID NO: 6.

6. A method as in claim 5 wherein said administration comprises application of said bone regeneration material to a periodontal site in the patient.

7. A method as in claim 5 wherein said administration comprises application of said bone regeneration material to a site in the patient in need of orthopedic repair.

8. A method as in claim 5 wherein said bone regeneration material is administered in combination with bone graft implant particles.

9. A method as in claim 5 wherein said material is applied to the patient during a surgical procedure at a site in need of orthopedic or periodontal repair.

10. A method as in claim 5 wherein said administration comprises topical application or injection of said bone regeneration material to a site on the patient in need of periodontal or orthopedic repair.

11. A method as in claim 5 wherein said administration comprises implantation of a medical device, wherein said device has said bone regeneration material applied to a surface thereof.

12. A method as in claim 11 wherein said device is a bone implant device.

* * * * *